Figure 1:
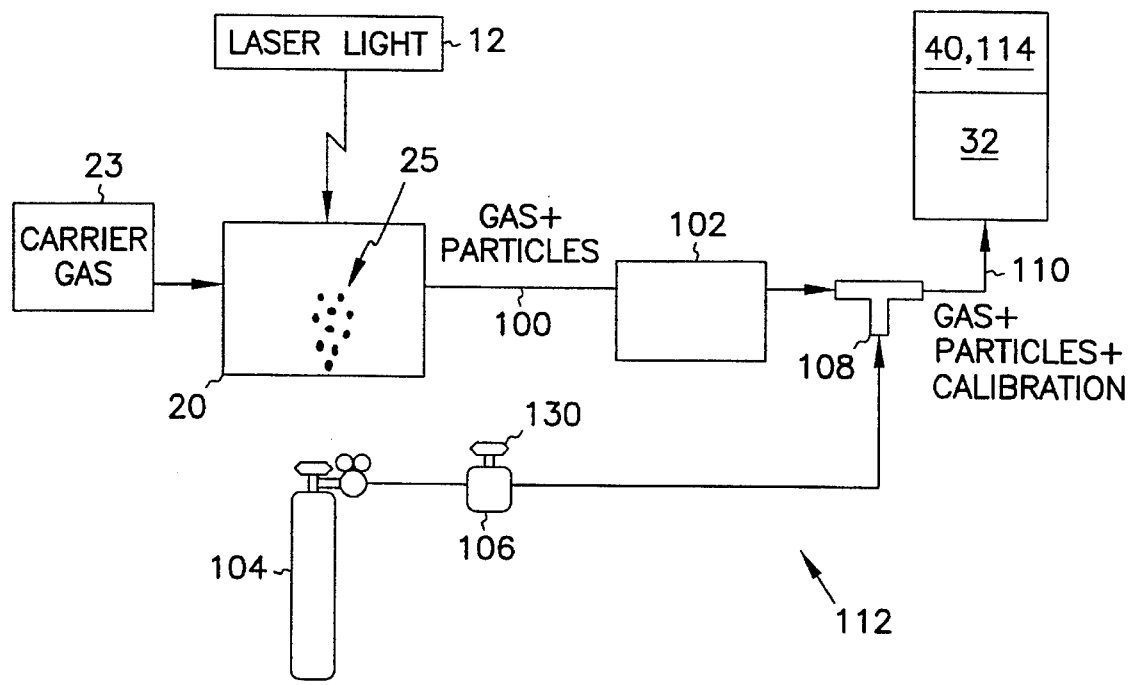
Figure 2:
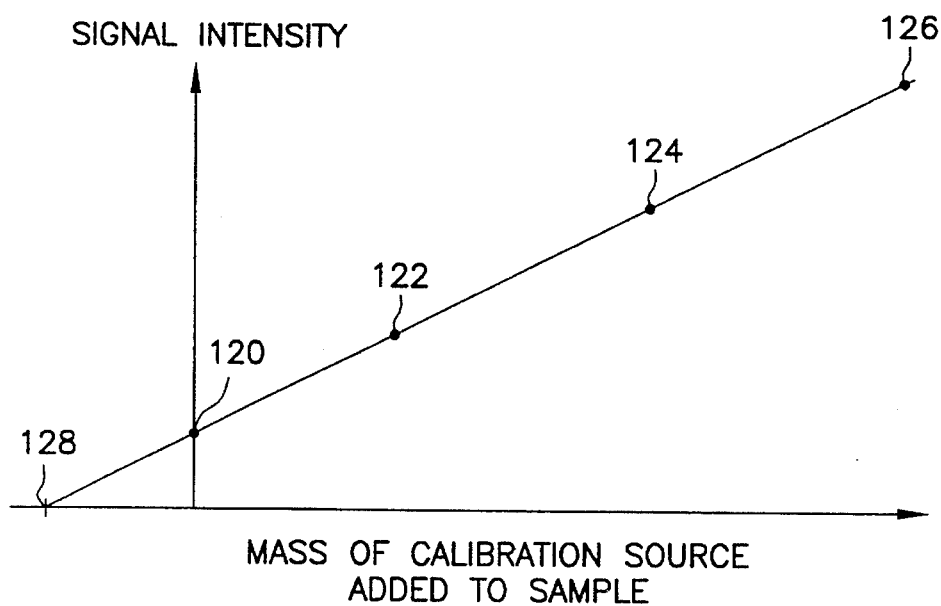

United States Patent [19]
Braymen

[11] Patent Number: 5,526,110
[45] Date of Patent: Jun. 11, 1996

[54] IN SITU CALIBRATION OF INDUCTIVELY COUPLED PLASMA-ATOMIC EMISSION AND MASS SPECTROSCOPY

[75] Inventor: Steven D. Braymen, Ames, Iowa

[73] Assignee: Iowa State University Research Foundation, Inc., Ames, Iowa

[21] Appl. No.: 273,024

[22] Filed: Jul. 8, 1994

[51] Int. Cl.$^6$ ................................................. G01N 21/73
[52] U.S. Cl. ....................... 350/316; 250/288; 250/252.1
[58] Field of Search ............................ 356/316; 250/288, 250/252.14

[56] References Cited

U.S. PATENT DOCUMENTS

| | | |
|---|---|---|
| 3,521,959 | 7/1970 | Fassel et al. . |
| 4,598,577 | 7/1986 | Jowitt et al. ................................. 356/36 |
| 4,802,761 | 2/1989 | Bowen et al. ............................ 356/301 |
| 4,986,658 | 1/1991 | Kim ............................................. 356/318 |
| 5,085,499 | 2/1992 | Griffin et al. .............................. 356/316 |
| 5,104,391 | 4/1992 | Ingle et al. ............................... 356/73.1 |

FOREIGN PATENT DOCUMENTS

| | | |
|---|---|---|
| 61-200446 | 5/1986 | Japan . |
| 93/07453 | 4/1993 | WIPO . |

OTHER PUBLICATIONS

Anal. Chem. 1994, 66, 1911–1917, "Aerosol Mass Measurement and Solution Standard Additions for Quantitation in Laser Ablation–Inductively Coupled Plasma Atomic Emission Spectrometry. David P. Baldwin, Daniel S. Zamzow, and Arthur P. D'Sliva" Ames Laboratory–U.S. Department of Energy, Ames, Iowa 50011.

Applied Spectroscopy, vol. 44, No. 3, 1990, pp. 373–380. "Studies of Aerosols generated by Electrically Vaporized thin Films for ICP–AES", Stephen W. Brewer, Jr., Ketan Trivedi, Frederick I. Braid, and Richard D. Sacks.

"Conceptual Robotic Soil Sampler using Remote ICP–AES Technology", pp. 153–158. May 29–30, 1991.

Applied Spectroscopy, vol. 44, No. 2, 1990, pp. 183–186. "An Efficient and Inexpensive Ultrasonic Nebulizer for Atomic Spectrometry", Qinhan Jin, Chu Zhu, Kevin Brushwyler, and Gary M. Hieftje.

*Primary Examiner*—F. L. Evans
*Attorney, Agent, or Firm*—Schwegman, Lundberg & Woessner

[57] ABSTRACT

A method and apparatus for in situ addition calibration of an inductively coupled plasma atomic emission spectrometer or mass spectrometer using a precision gas metering valve to introduce a volatile calibration gas of an element of interest directly into an aerosol particle stream. The present situ calibration technique is suitable for various remote, on-site sampling systems such as laser ablation or nebulization.

18 Claims, 3 Drawing Sheets

IN SITU CALIBRATION OF INDUCTIVELY COUPLED PLASMA-ATOMIC EMISSION AND MASS SPECTROSCOPY

STATEMENT OF GOVERNMENT RIGHT

This invention was made with support of the U.S. Government under United States Department of Energy Contract No. W-7405-ENG-82. The Government has certain rights in the invention.

BACKGROUND OF THE INVENTION

1. Field of the Invention

The present invention relate to a method and apparatus for the in situ addition calibration of an inductively coupled plasma atomic emission spectrometer or mass spectrometer using a precision gas metering valve to introduce a volatile calibration gas of an element of interest directly into an aerosol particle stream, and in particular, use of the present in situ calibration technique with various remote, on-site sampling systems.

2. Description of the Related Art

Inductively coupled plasma atomic emission spectrometers and mass spectrometers can be calibrated by adding a series of standardized additions to the sample being tested. A standard addition curve for the analyte being measured can then be generated. However, in some circumstances it is difficult or not possible to add the standards to the sample.

For example, there is an ongoing need to sample and analyze dangerous or hazardous materials, or materials located in hazardous environments such as soil or water at hazardous waste sites (radioactive wastes, toxic chemical dumps or contaminated structures) or molten metals in a manufacturing foundry. Conventionally, a sample of a hazardous waste is removed from the site and brought to a laboratory for analysis. The sample must therefore be carefully extracted, transported, handled and stored in order to assure the safety of the technicians carrying out the test, as well as the public. The expense and delay entailed in extracting, handling and storing such materials, as well as the health risks, have encouraged scientists to develop alternative testing approaches minimizing these disadvantages.

The Iowa State University Research Foundation has developed a system for analyzing the composition of specimens directly at a sample site. This system is disclosed in a U.S. patent application Ser. No. 08/117,242, entitled MOBILE INDUCTIVELY COUPLED PLASMA SYSTEM, filed by A. D'Silva and E. Jaselskis, and further disclosed in published PCT application No. WO 93/07453, both of which are hereby incorporated by reference. However, the amount of a sample delivered to the inductively coupled plasma (ICP) or mass spectrometer varies with laser output power and power density at the sample surface, light scattering from aerosol particles in the ablation cell, and variations in aerosol transport out of the cell and through the transfer tubing to the ICP torch.

In order to quantitate and normalize on-site samples, a method and apparatus for determining in situ the mass and concentration of elements of interest is needed for use with inductively coupled plasma atomic emission spectrometers (LA-ICP-AES) and a mass spectrometers. Various methods for normalization and quantitation in laser ablation sampling are described in D. Baldwin, D. Zamzow, and A. D'Silva, "Aerosol Mass Measurement and Solution Standard Additions for Quantitation in Laser Ablation-Inductively Coupled Plasma Atomic Emission Spectrometry", 55 *Anal. Chem.* 1911, 1917 (1994), which is hereby incorporated by reference.

The method disclosed in the above noted article combines the technique of aerosol mass measurement and solution standard additions. A portion of the laser-ablated sample aerosol is diverted to a quartz microbalance and the mass flow rate is measured. During the laser ablation sampling process, a measured amount of a desolvated aerosol obtained from ultrasonic nebulization of solution standards is added to the laser-ablation aerosol to generate a standard addition curve for the analyte being determined.

However, ultrasonic nebulizers are not 100% efficient. Failure to nebulize all of the liquid in the standard will introduce error into the system. Nebulization may also be effected by temperature and pressure. Additionally, the liquid standards utilized with this technique typically contain dangerous concentrations of acids and can be unstable over time. Finally, the overall complexity of the pumps and valves necessary to introduce the nebulized standard into the ablation stream are not well suited to automation and may impact on the reliability of the system.

SUMMARY OF THE INVENTION

The present invention relates to a method and apparatus for the in situ addition calibration of an inductively coupled plasma atomic emission spectrometer or inductively coupled plasma mass spectrometer using a precision gas metering valve to introduce a volatile calibration gas of an element of interest directly into an aerosol particle stream.

In the preferred embodiment, the aerosol mass is measured alone. A series of calibration gas standards of known quantity are then added to the aerosol particle stream to generate a standard addition curve for the analyte, so that the mass and concentration of the analyte in the sample can be determined.

The preferred method involves diverting a portion of the particle stream to amass flow rate measuring system. The mass concentration of the aerosol is measured so that the analytical signal can be normalized for the amount of the sample introduced into the ICP. A precision gas metering valve is used to introduce a series of accurately measured specimens of different quantities of a volatile calibration gas of an element of interest into the aerosol particle mass stream. The combined calibration gas/particle mass stream then passes to an ion-coupled plasma torch where the particles are vaporized, atomized, and ionized to emit their characteristic emissions of optical radiation and ions of the elemental constituents. The intensity of the emissions from the test specimens are plotted on one axis and the quantity of calibration gas added is plotted on the other axis. The resulting plot can be extrapolated to determine the mass of the element of interest.

For the mass spectroscopy embodiment, the ions are counted by the instrument directly. When accurately measured quantities of the elements of interest are added to the particle stream in varying quantities, a plot of ion intensity versus quantity added can be dram. Extrapolating the plot to the x-axis reveals the original concentration of the element of interest.

The combination of the volatile calibration gas and the laser-ablation aerosol generates a standard addition curve for the analyte being measured. The standard addition procedure corrects for potential plasma related matrix effects in the ICP emission signal, allowing only one standard test sample for calibration without the need for an internal standard in the samples.

The volatile calibration gas maybe introduced to the particle stream anywhere between the sample location and the ICP or mass spectrometer, depending upon the configuration of the system.

According to one aspect of the invention, a remotely controlled mobile cart positions a probe proximate to the sampling site. A high energy wavelength laser ablates the material, forming a cloud of micron-sized particles. The particles are drawn from the sampling site by an aerosol system which employs an inert gas, such as argon. Prior to the sample particles and the carrier gas being injected into an ICP source, a volatile calibration gas is introduced to the particle stream. The resulting electromagnetic radiation can be analyzed with an optical spectrometer to determine the concentration of the element of interest. Alternatively, an ultrasonic nebulizer may be substituted for the laser ablation system.

BRIEF DESCRIPTION OF THE DRAWINGS

FIG. 1 is a schematic illustration of the present in situ calibration process utilizing a volatile gaseous standard;

FIG. 2 is an exemplary graphical illustration of the addition calibration technique of the present invention;

FIG. 3 provides a schematic illustration of an exemplary mobile inductively coupled plasma system;

FIG. 4 illustrates an exemplary application of the mobile inductively coupled plasma system for sampling soil at a hazardous waste site; and FIG. 5 is a schematic illustration of an exemplary mobile inductively coupled plasma system utilizing an ultrasonic nebulizer rather than laser ablation to extract a sample.

DETAILED DESCRIPTION OF THE PREFERRED EMBODIMENT

FIG. 1 is a schematic illustration of the preferred in situ calibration system for an inductively coupled plasma atomic emission spectroscope 32, 40 (ICP-AES) or an inductively coupled plasma mass spectroscope 32, 114 using a precision gas metering valve. A carrier gas 23 forces a carrier gas/particle stream 100 from an ablation cell 25 to a quartz microbalance 102. In the preferred embodiment, 5% to 15% of the carrier gas/particle stream 100 is analyzed by the quarts microbalance 102, while the remainder of the combined stream bypasses quarts the microbalance 102. The mass flow rate is determined based on the proportion of the carrier gas/particle stream flow diverted. The preferred quarts microbalance 102 consists of a piezoelectric microbalance mass sensor with an electrostatic precipitator to deposit aerosol particles onto the sensor.

In an alternative embodiment, the entire carrier gas/particle stream 100 is analyzed by the quarts microbalance 102 for a period of time. The quarts microbalance 102 is then bypassed for the calibration phase of the analysis. The mass flow rate of the carrier gas/particle stream 100 is assumed to remain constant for the calibration phase of the analysis.

A volatile calibration gas 104 is metered through a precision metering valve 106 and mixed with the carrier gas/particle stream 100 in a mixing valve 108 by the calibration system 112. The metering valve 106 allows the mass flow rate of the calibration gas 104 to be accurately controlled and measured. The calibration gas preferably is a volatile compound of the element of interest. For example, silicon is a good baseline for soil samples between sites. If silicon is the element of interest, the calibration gas 104 can be silicon tetrachloride.

The combined carrier gas/particle stream/calibration gas 110 is directed to an inductively coupled plasma system (ICP) 32. The ICP 32 vaporizes, atomizes, and ionizes the particle stream and calibration gas to emit characteristic emissions of optical radiation or ions of the elemental constituents. The element of interest can be isolated and quantified. The intensity of the emission from the element of interest is proportional to the quantity of the element present in the sample. If an atomic emission spectrometer 40 is used, the electromagnetic radiation from the ICP 32 is analyzed. Alternatively, a mass spectrometer can be used to analyze ions from the ICP 32.

A stepper motor 130 maybe added to the metering valve 106 to allow both manual and computer control of the valve 106. The preferred metering valve is available from Vacuum Accessories Corp. of America, under the model number SMC-102A. However, it will be understood that a variety of metering valves are available which are suitable for this purpose.

FIG. 2 is an exemplary graphical illustration of the addition calibration technique of the present invention in which the mass of calibration gas 104 added is plotted on the x-axis and the signal intensity of an atomic emission spectroscope or mass spectroscope is plotted on the y-axis. The signal intensity for the carrier gas/particle stream 100 without the calibration gas 104 is shown at point 120. Varying amounts of the calibration gas 104 are added to the carrier gas/particle stream 100. The output signal intensity from the atomic emission spectrometer 40 or mass spectrometer 114 vary proportionally to combined quantity of the element of interest present in the aerosol stream 100 and the calibration gas 104. The signal intensity for each quantity of calibration gas 122, 124, 126 are also plotted. The x-axis intercept 128 represents the amount of mass of the element of interest in the original sample 25. The mass flow rate measured by the quarts microbalance 102 is used to determine the actual concentration of the element of interest.

If a mass spectrometer 114 is substituted for the atomic emission spectroscope 40, the ion intensity is plotted on the y-axis and the mass of calibration gas added to the sample is plotted on the x-axis. Multiple accurately measured quantities of the elements of interest are added to the particle stream in varying quantities so that a plot of ion intensity versus quantity added can be drawn. Extrapolating the plot to the x-axis reveals the original concentration of the element of interest.

For example, if the element of interest is silicon, silicon tetrachloride can be the calibration gas. The metering valve from Vacuum Accessories Corp. of America can meter as low as $1\times10^{-10}$ std. cc/sec. Silicon tetrachloride has a density of $7\times10^{-3}$ g/cc which corresponds to $1.7\times10^{-13}$ g/sec silicon. If the sample from a 3 minute ablation totaled 1 nanogram, the rate of ablation would be on the order of $5.6\times10^{-12}$ g/sec, which is approximately thirty (30) times the minimum metering rate of the valve. The resulting error rate being less than 3%.

The present in situ calibration system may be used with any inductively coupled plasma atomic emission spectrometer or mass spectrometer in which a volatile calibration gas of an element of interest can be metered directly into an aerosol particle stream. While the on-site sampling systems disclosed herein are an important application for the present invention, it will be understood that the present invention is not limited to such use.

Figure 3:
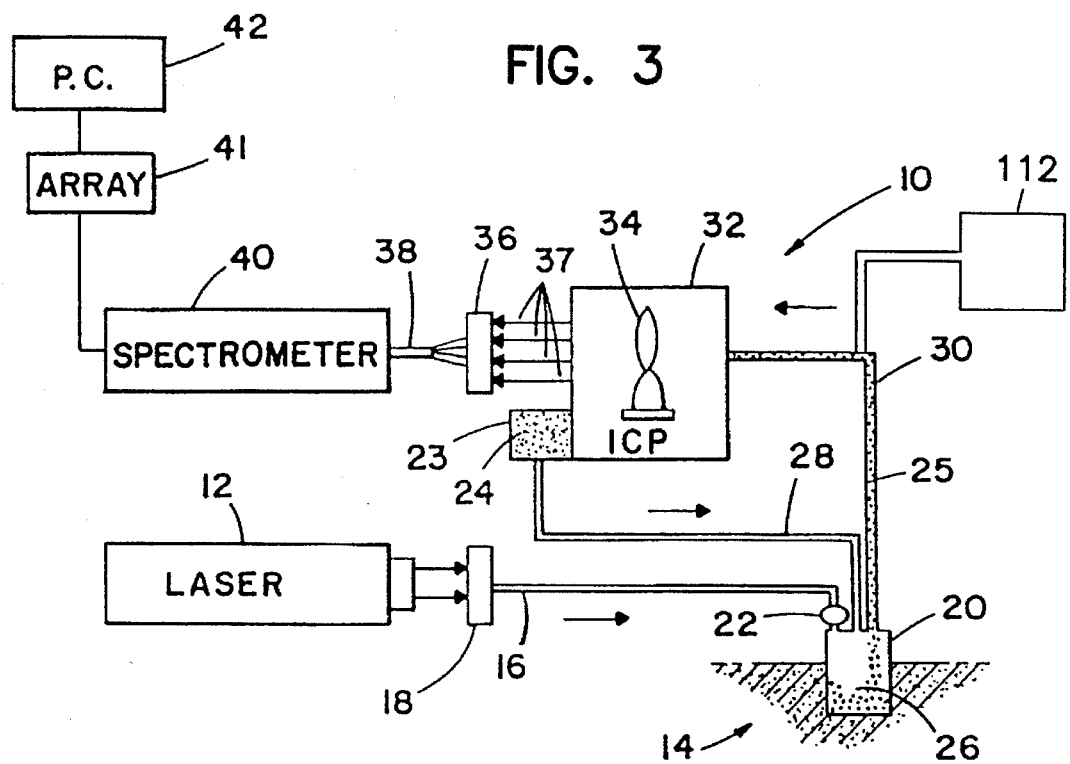

FIG. 3 provides a simplified schematic illustration of an exemplary mobile inductively coupled plasma system 10 for on site sampling. Laser radiation from a laser 12 is directed to the sampling site 14 through fused silica fiber optics 16. The exemplary laser provides continuous or pulsed, fixed wavelength laser radiation at least three different wavelengths, 1064 nm, 532 nm, and 355 nm. These wavelengths are chosen to provide a range of energies as materials to be analyzed have different absorption characteristics at different wavelengths. Since current optical fibers are subject to damage at wavelengths below 350 nm and power levels of $10^8$ watts/cm²/sec., it is best to utilize laser wavelengths above 350 nm when using a fiber optic delivery system. These constraints will change with the availability of better optical fibers. As most materials absorb optical radiation in the ultraviolet, ablation is more efficiently carried out at wavelengths below 400 nm. The Lumonics Dye Laser (Hyper-Dye 300) pumped by the Lambda Physik Excimer Laser (model EMG102MSC) is known to provide laser beams suitable, although the preferred system for field operation is the solid state YAG laser.

A laser focusing system 18 is provided to focus the laser output onto the optical fiber 16, without reaching overload. Polymicro Technologies fiber optics cable model FVPS600660690 is known to be suitable for carrying the laser radiation to a ablation cell 20, provided no more than $10^8$ watts/cm²/sec. is applied to the head end of the fiber. As noted above, power levels in excess of this can damage the fiber. Focusing system 18 may include a filter to narrow the laser beam and reduce the power actually received by the optical fiber and a series of lenses to focus the laser radiation onto the end of the optical fiber.

The ablation cell 20 has optics 22 for focusing the laser radiation from the fiber 16 on the material to be sampled 14. The ablation cell 20 is generally constructed of aluminum, but other materials maybe preferable to contend with different environmental conditions. A carrier gas source 23 preferably supplies argon gas 24 to a ablation cell sampling chamber 26 through an aerosol input line 28, however other gases may be suitable for this purpose with the appropriate ICP. The material ablated or sampled 25 by the laser radiation mixes with the argon 24 to form an aerosol which is drawn from the ablation cell sampling chamber 26 through the aerosol output line 30 to the inductively coupled plasma (ICP) source 32. Argon 24 is the support gas for the ICP 32. The present invention employs an RF Plasma Products® inductively coupled argon plasma system.

The aerosol is directed into the plasma source 34, through an output line 30 to the ICP 32. The energized sample particles are vaporized, atomized, and ionized to provide characteristic optical reduction of the elemental constituents of the sample 25 in the form of electromagnetic radiation 37, which is focused by a lens 36 and thereby subsequently channeled through an ICP output optical cable 38 to a multi-channel or sequential optical spectrometer 40. Alternatively, the laser light may be directly delivered to the spectrometer 40. The present calibration system 112 is located upstream of the ICP 32.

To carry the optical output of the ICP 32 to the spectrometer 40, the preferred embodiment of the present invention employs Polymicro Technologies fiber optic bundle (model PTA-EI0019FF-030-0DP), consisting of 19 separate 200 μm core diameter fibers arranged in a round-to-linear bundle. The Acton Research Corp. 0.5 meter spectrometer (model VM-505) equipped with a 2400 grooves/mm grating has been found suitable as the spectrometer. The optical radiation dispersed in the spectrometer is detected by a multi-channel diode array detector 41. The EG&G Princeton Applied Research intensified diode array (model 1420) and diode array controller (model 1463) are known to be suitable for this purpose. Preferably, the IEEE output of the detector 41 is connected to a personal computer 42 or work station whereby the output of the spectrometer 40 can be stored, enhanced, processed, analyzed, and displayed.

Figure 4:
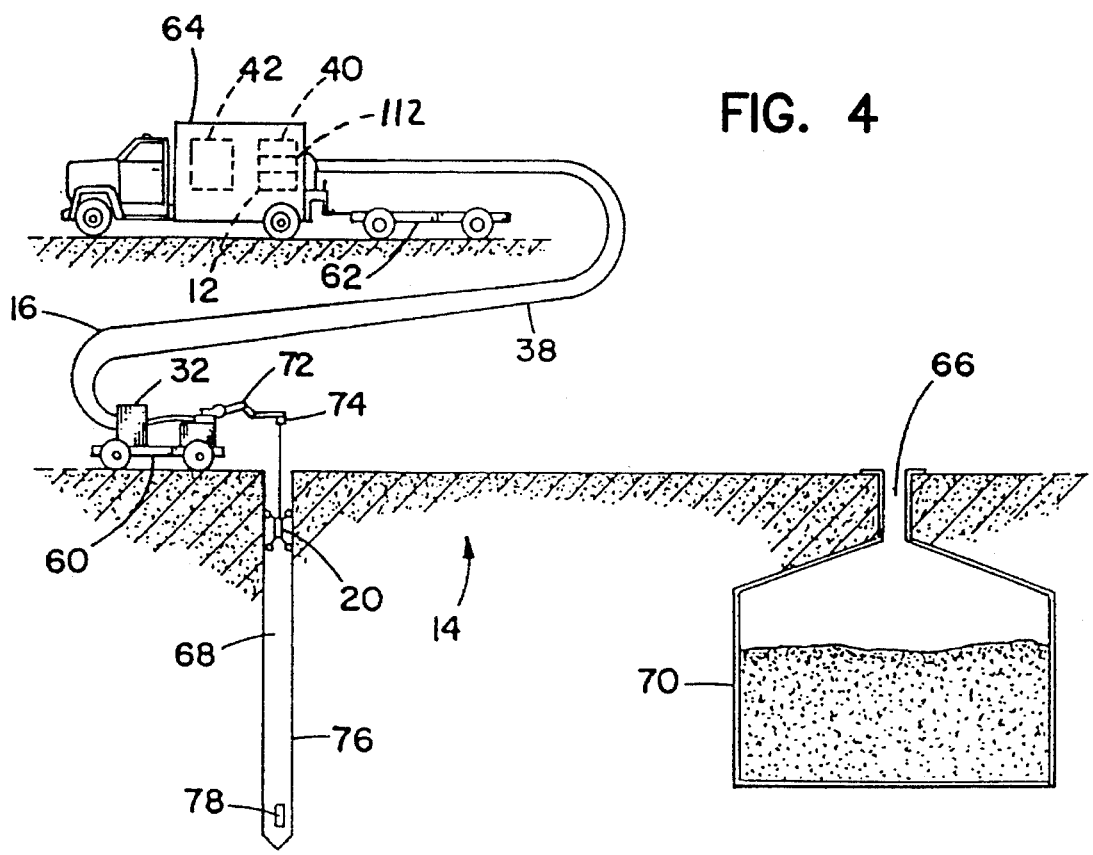

FIG. 4 illustrates an exemplary embodiment of the mobile inductively coupled plasma system 10. A remotely controlled mobile cart 60 is carried on a trailer 62 behind a truck 64. The truck 64 contains a power source for operating the components of the system. In use, the truck 64 is positioned a distance from the toxic waste sampling site 14. The remotely controlled mobile cart 60 is then positioned proximate to the sampling site 14, for instance a sampling bore 68 adjacent to the toxic waste storage chamber 70, by direct visual reckoning or by use of video images relayed from a video camera (not shown) mounted on the cart 60. The controls for maneuvering cart 60 are located in the truck 64.

The remotely controlled mobile cart 60 carries the ICP source 32, so that the ICP source is as close to the sampling site 14 as possible, thereby minimizing the distance the hazardous material needs to be transported in the aerosol output line 30 and to keep the hazardous material away from the operators positioned in the truck 64.

The aerosol tubes 28 and 30 are 0.25" in diameter, made of Teflon® or polyethylene material, and are pressurized to provide a gas flow of 1.0 liters/minute. The argon 24 is held under pressure in the argon source 23 to provide pressure to the system. Transportation of material samples 25 in the aerosol line 30 to a distance of 100 feet has been achieved.

The laser source 12, spectrometer 40, and present calibration system 112 are located in the truck 64. As explained above with respect to FIG. 3, an optical fiber 16 carries the laser beam from the laser 12 to the ablation cell 20, while a second fiber 38 carries the output of the ICP 32 to the spectrometer 40. Using the equipment specified herein, the laser beam can be carried up to 30 meters on the fiber 16. Similarly, fiber 38 can carry the output of the ICP 32 about 30 meters to the spectrometer 40.

The ablation cell 20 is attached to a three-axis robot arm 72 mounted to the cart 60, which is also controlled remotely by the operator, preferably using images relayed from a video camera mounted on the platform or even on the probe itself. The operator controls the robot arm 72 to position the ablation cell 20 over the center of the sampling bore 68. The tubes 28 and 30 and fiber 16, a load-bearing cable 73, and other necessary electronic cables (not shown) are wound on a spool with a winch 74, which is remotely controlled to lower and raise the ablation cell 20. The sampling bore 68 contains a liner 76 (shown in more detail in FIG. 3), which can be a conventional pipe with a cut-out area, or window 78, through which access to the sampling site 14 is obtained.

The ablation cell 20 is lowered into the sampling bore 68 until it is adjacent to the sampling window 78. The sampling thus proceeds with the operators at a safe distance from the sampling site 14. When sampling is completed, the probe 20 is withdrawn from the sampling bore 68 and the remotely controlled mobile cart 60 is returned to the trailer 62 for transportation to the next site. If any contamination has occurred, it is generally limited to the ablation cell 20 or the immediate accessories (i.e., cables, etc.), allowing relatively easy clean-up. The sample 25 itself is incinerated in the ICP plasma source 34. If necessary, the ablation cell 20 and accessories can be disposed of or destroyed and replaced at relatively low cost. Further information on laser ablation is set forth in the paper entitled "Laser Vaporization in Atomic Spectroscopy," by H. K. Dittrich and R. Wennrich, *Prog. Analyt. Spectrosc.*, 7, 139–198 (1984), the entire contents of which are hereby incorporated by reference herein.

Figure 5:
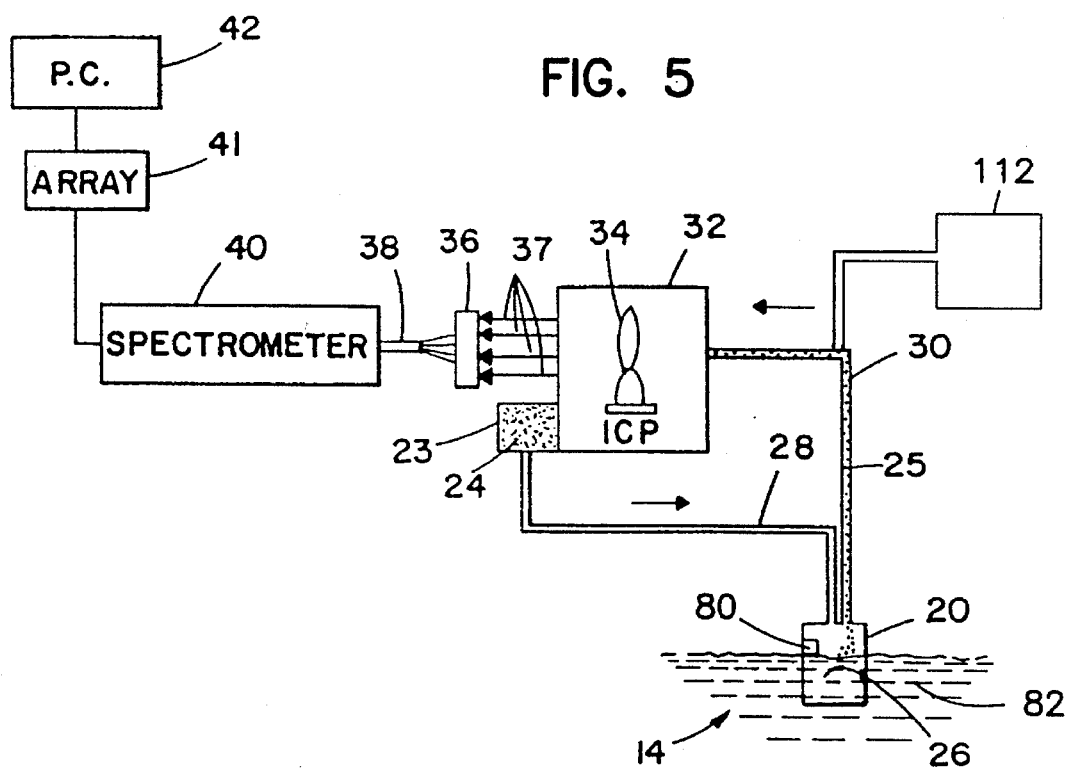

FIG. 5 illustrates an alternate exemplary on-site sampling system using an ultrasonic nebulizer 80 produce an aerosol 25 from liquid material 82 instead of the laser 12 to ablate a sample. In principle, when ultrasonic waves from a transducer 80 of sufficient frequency and amplitude are produced, a capillary wave action is induced in a liquid medium 82, causing the ejection of aerosol droplets from the liquid surface. The droplets, the dimensions of which are dependent on the ultrasonic frequency and physical properties of the liquid, can be produced with micron sized diameters. By synchronizing the transducer 80 frequencies and focusing the ultrasonic waves to a single point, a wave pattern should be generated with an amplitude sufficient to provide the quantities of sample 25 required for ICP 32 analysis. A low frequency, high power, ultrasonic stephorn generator known to be suitable for the present embodiment is disclosed by Fassel and Dickinson, *Anal. Chem*, 40, 1968, 247; and in U.S. Pat. No. 3,521,949. Once a representative aerosol sample 25 is generated, it mixes with the argon 24 and is transported to ICP 32 for analysis. The nebulized liquid material 82 is drawn through the aerosol output line 30 to the ICP 32. Sample analysis proceeds as discussed in connection with FIG. 1, except that the laser 12 is replaced by the nebulizer 80.

It will be understood that the above on-site sampling systems are disclosed by way of example only and that the present in situ calibration system may be used with any on-site sampling system, including an ordinary nebulizer in which the sample passes through an aerosol nozzle.

It is to be understood that the above description is intended to be illustrative, and not restrictive. Many other embodiments will be apparent to those of skill in the art upon reviewing the above description. Although the above inventions have been described in connection with a laser ablation system, it should be apparent that the concepts extend to an ultrasonic nebulizer or any other sample generation technique. The scope of the invention should, therefore, be determined with reference to the appended claims, along with the full scope of equivalents to which such claims are entitled.

I claim:

1. An apparatus for determining the concentration of an element of interest in a sample contained in an aerosol stream, comprising:

an inductively coupled plasma spectrometer for vaporizing, atomizing, and ionizing at least the element of interest to emit characteristic emissions, the emissions generating an output signal in the spectrometer with an intensity proportional to the quantity of the element of interest;

an aerosol delivery system for delivering the aerosol stream to the inductively coupled plasma spectrometer, the aerosol stream containing a carrier gas and the element of interest;

means for measuring the mass flow rate of the aerosol stream;

a volatile calibration gas compound of the element of interest; and a precision gas metering valve for introducing a series of known quantities of a volatile calibration gas directly into the aerosol stream, the metering valve determining the mass flow rate of the calibration gas and the spectrometer generating an output signal intensity proportional to the quantity of calibration gas and element of interest present in the aerosol so that a standard addition curve of the intensity versus the quantity of calibration gas added can be generated to determine the concentration of the element of interest in the sample.

2. The apparatus of claim 1 wherein the means for measuring the mass flow rate of the aerosol stream is a quartz microbalance.

3. The apparatus of claim 1 further including sample collection means for extracting at least the element of interest from a sample site and introducing at least the element of interest into the aerosol stream.

4. The apparatus of claim 3 wherein the sample collection means comprises a laser ablation system.

5. The apparatus of claim 3 wherein the sample collection means comprises a nebulizer.

6. The apparatus of claim 1 further including a stepper motor for activating the precision gas metering valve.

7. The apparatus of claim 1 wherein the characteristic emissions comprise ions and the spectrometer comprises a mass spectrometer.

8. The apparatus of claim 1 wherein the characteristic emissions comprise electromagnetic radiation and the spectrometer comprises an atomic emission spectrometer.

9. An apparatus for determining the concentration of an element of interest collected at a remote sampling site, comprising:

an inductively coupled plasma spectrometer for vaporizing, atomizing, and ionizing at least the element of interest to emit characteristic emissions, the emissions generating an output signal intensity proportional to the quantity of the element of interest in the sample;

a laser proximate the sampling site;

a first optical fiber with first and second ends, the first end coupled to the laser and the second end positioned proximate the remote sampling site for directing a laser beam from the laser onto a surface of the sampling site to abate a sample of at least the element of interest;

an aerosol delivery system containing a carrier gas for delivering at least the element of interest to the inductively coupled plasma spectrometer where at least the element of interest is dissociated, atomized and excited to provide its characteristic optical emissions;

a volatile calibration gas compound of the element of interest; and a precision gas metering valve for introducing a series of known quantities of a volatile calibration gas directly into the aerosol stream containing at least the element of interest, the metering valve determining the mass flow rate of the calibration gas and the spectrometer generating an output signal intensity proportional to the quantity of calibration gas and element of interest present in the aerosol so that a standard addition curve of the intensity versus the quantity of calibration gas added can be generated to determine the concentration of the element of interest in the sample.

10. A method for determining the concentration of an element of interest in a sample contained in an aerosol stream, comprising the steps of:

providing an inductively coupled plasma spectrometer for vaporizing, atomizing, and ionizing at least the element of interest to emit characteristic emissions, the spectrometer generating an output signal intensity proportional to the quantity of the element of interest in the sample;

providing an aerosol delivery system for delivering the aerosol stream to the spectrometer;

measuring them ass flow rate of the aerosol stream;

introducing a series of known quantities of a volatile calibration gas of the element of interest directly into the aerosol stream using a precision gas metering valve, the spectrometer generating an output signal intensity proportional to the quantity of calibration gas and element of interest present in the aerosol stream;

determining the mass flow rate of the calibration gas; and generating a standard addition curve of the output signal intensity versus the quantity of calibration gas added to determine the concentration of the element of interest in the sample.

11. The method of claim 10 wherein the characteristic emissions comprise ions and the spectrometer comprises a mass spectrometer.

12. The method of claim 10 wherein the characteristic emissions comprise electromagnetic radiation and the spectrometer comprises an atomic emission spectrometer.

13. The method of claim 10 further including the step of comparing the mass flow rate of the element of interest with the mass flow rate of the aerosol stream to determine the concentration of the element of interest in the sample.

14. The method of claim 10 wherein the step of measuring the mass flow rate of the aerosol stream comprises diverting a portion of the aerosol stream to a means for measuring mass flow rate.

15. The method of claim 10 wherein the step of measuring the mass flow rate of the aerosol stream comprises diverting the entire aerosol stream to a means for measuring mass flow rate prior to introducing the calibration gas.

16. The method of claim 10 further including the step of:

providing sample collection means for extracting at least the element of interest from a sample site; and introducing at least the element of interest into the aerosol stream.

17. The method of claim 16 wherein the sample collection means comprises a laser ablation system.

18. The method of claim 16 wherein the sample collection means comprises a nebulizer.

* * * * *

UNITED STATES PATENT AND TRADEMARK OFFICE
CERTIFICATE OF CORRECTION

PATENT NO. : 5,526,110

DATED : June 11, 1996

INVENTOR(S) : Steven D. Braymen

It is certified that error appears in the above-identified patent and that said Letters Patent is hereby corrected as shown below:

Column 2, line 41, delete "amass" and insert therefor --a mass--.

Column 2, line 61, delete "dram" and insert therefor --drawn--.

Column 3, line 4, delete "maybe" and insert therefor --may be--.

Column 3, line 49, delete "quarts" and insert therefor --quartz--.

Column 3, line 53, delete "quarts" and insert therefor --quartz--.

Column 3, line 57, delete "quarts" and insert therefor --quartz--.

Column 3, line 58, delete "quarts" and insert therefor --quartz--.

Column 4, line 41, delete "quarts" and insert therefor --quartz--.

Column 9, line 6, delete "them ass" and insert therefor --the mass--.

Signed and Sealed this

Seventh Day of January, 1997

Attest:

BRUCE LEHMAN

*Attesting Officer*    *Commissioner of Patents and Trademarks*